United States Patent [19]

Ghebre-Sellassie et al.

[11] Patent Number: 5,358,723
[45] Date of Patent: Oct. 25, 1994

[54] PROCESS AND COMPOSITION FOR THE DEVELOPMENT OF CONTROLLED RELEASE GEMFIBROZIL DOSAGE FORM

[75] Inventors: Isaac Ghebre-Sellassie, Morris Plains; Uma Iyer, Mendham, both of N.J.

[73] Assignee: Warner-Lambert Company, Morris Plains, N.J.

[21] Appl. No.: 57,203

[22] Filed: May 4, 1993

Related U.S. Application Data

[63] Continuation of Ser. No. 798,275, Nov. 26, 1991, abandoned.

[51] Int. Cl.⁵ ............................................. A61K 9/14
[52] U.S. Cl. .................................... 424/485; 424/470; 424/490; 424/497
[58] Field of Search ................ 424/489, 490, 497, 470

[56] References Cited

U.S. PATENT DOCUMENTS

| | | | |
|---|---|---|---|
| 4,810,501 | 3/1989 | Ghebre-Sellassie | 424/470 |
| 4,925,676 | 5/1990 | Ghebre-Sellassie | 424/497 |
| 4,927,639 | 5/1990 | Ghebre-Sellassie | 424/497 |
| 4,971,804 | 11/1990 | Ghebre-Sellassie | 424/490 |
| 5,102,668 | 4/1992 | Eichel et al. | 424/490 |

FOREIGN PATENT DOCUMENTS

| | | |
|---|---|---|
| 0297866 | 1/1989 | European Pat. Off. |
| 9100085 | 1/1991 | WIPO |

OTHER PUBLICATIONS

Chemical Abstracts, vol. 80, No. 2, 10 Jul. 1958, Columbus, Ohio; abstract No. 12095k, Nixon, J. R. et al. "Release of Drugs from Suspended and Tabletted Microcapsules," p. 367; col. 2.

*Primary Examiner*—Thurman K. Page
*Assistant Examiner*—William E. Benston, Jr.
*Attorney, Agent, or Firm*—Michael J. Atkins

[57] ABSTRACT

Gemfibrozil formulations prepared from a single granulation of gemfibrozil and a release-control agent are disclosed. The release-control agent is present in an amount sufficient to provide both immediate and controlled release of gemfibrozil. A method of preparing the formulation and a compressed tablet are also disclosed.

11 Claims, No Drawings

PROCESS AND COMPOSITION FOR THE DEVELOPMENT OF CONTROLLED RELEASE GEMFIBROZIL DOSAGE FORM

This application is a continuation of 07/798,275 filed Nov. 26, 1991 now abandoned.

BACKGROUND OF THE INVENTION

The present invention relates to controlled release gemfibrozil formulations. In particular, the present invention is directed to formulations having both immediate and controlled release of gemfibrozil.

Gemfibrozil, or 5-(2,5-dimethylphenoxy)-2,2-dimethylpentanoic acid, is a widely used antihyper-lipoproteinemic agent. While apparently absorbed throughout the gastrointestinal tract, maximum absorption appears to occur in the upper gastrointestinal tract, notwithstanding the poor solubility of the drug at acidic pH's.

In recent years, for patient convenience, it has become desirable to provide controlled release formulations. In self-medicating patients, where efficacious blood serum levels of the active ingredient are imperative, controlled release formulations are particularly useful. In addition, controlled release formulations are useful for those patients who may easily forget to take medication.

One solution for providing controlled and/or extended release of gemfibrozil is set forth in commonly-assigned U.S. Pat. No. 4,925,676. This reference discloses a compressed disintegratable tablet prepared from a gemfibrozil formulation containing a mixture of two separate granulations. The first granulation is prepared with at least one acid-disintegratable binder while the second granulation is prepared by regranulating the first granulation with an alkali-disintegratable ingredient.

An alternative solution for providing extended release of gemfibrozil is set forth in commonly-assigned U.S. Pat. No. 4,927,639. This patent discloses a compressed tablet containing a disintegratable formulation of gemfibrozil prepared from a mixture of a first and second granulation. The first granulation contains finely divided particles of pure gemfibrozil granulated with at least one cellulose derivative. The second granulation contains finely divided particles of pure gemfibrozil granulated with a pharmaceutically acceptable water soluble or insoluble polymer which are then uniformly coated with a pharmaceutically acceptable methyl (meth) acrylate copolymer.

In spite of the above-described efforts, it would be advantageous to provide immediate and controlled release gemfibrozil formulations which do not require the labor and production costs associated with preparing multiple granulations. The ability to provide a single granulation which accomplishes both release patterns would result in savings in both time and manpower.

It is therefore an object of the present invention to provide a formulation of gemfibrozil prepared from a single granulation which provides a loading dose and controlled release of the therapeutic agent.

SUMMARY OF THE INVENTION

In accordance with the present invention, an improved formulation of gemfibrozil can be prepared from a single granulation which provides a loading dose and controlled release of gemfibrozil. The formulation is prepared by contacting gemfibrozil particles, preferably finely divided particles, with a release-control agent. The release-control agent is present in an amount whereby immediate release of free or partially-free active takes place as well as controlled release.

The release-control agent may be selected from acrylic acid series polymers, acrylic acid series copolymers and other substantially acid-insoluble alkali soluble polymers such as cellulose phthalates, poly(meth)acrylic acids and the like. In a preferred embodiment the release-control agent is dispersed or suspended in an aqueous solution. A particularly preferred release-control agent is Aquacoat® ECD 30, an aqueous suspension of ethyl cellulose containing 30% solids.

The ratio of gemfibrozil to the release-control agent is key to obtaining the desired release pattern. The overall ratio which provides free or partially-free active and controlled active is from about 11:0.5 to about 11:5 by weight. In a preferred embodiment, the ratio of the active, such as gemfibrozil, to the release-control agent is from about 11:0.75 to about 11:3 by weight, while in a most preferred embodiment, the ratio is from about 11:0.85 to about 11:1.25 by weight.

In one embodiment, gemfibrozil particles are blended with an excipient such as microcrystalline cellulose or lactose prior to the particles being contacted with the release-control agent.

In a further embodiment there is also provided a method of preparing the above-described formulation which includes contacting gemfibrozil particles, which are preferably finely divided, with a sufficient amount of a release-control agent to provide both immediate (e.g., free or partially free active) and release-controlled active. In a preferred method, the release-control agent is present as an aqueous suspension or dispersion, while the active and release-control agent are contacted for use in the formulation by granulating.

A method of preparing a compressed tablet having both immediate and controlled release of gemfibrozil is also provided.

As a result of the present invention there is provided a gemfibrozil formulation having both immediate and controlled release properties that offers time and labor savings when compared to formulations requiring the preparation of multiple granulations. The single granulation also overcomes uniformity problems associated with blending and compressing separate immediate and sustained release granules into tablets.

For a better understanding of the present invention, together with other and further objects, reference is made to the following description, the scope of which will be pointed out in the appended claims.

DETAILED DESCRIPTION OF THE INVENTION

In accordance with the present invention there is provided a formulation which includes gemfibrozil particles contacted with a release-control agent in an amount sufficient to provide a loading dose and controlled release of the active.

The contacting of the gemfibrozil with the release-control agent is preferably carried out by granulation techniques known in the art. For example, the granulation may be performed by agitation type apparatus, rotation type apparatus, centrifugal type apparatus, fluidized bed-type apparatus, or the like. The gemfibrozil, preferably in the form of finely divided particles, can be granulated either alone or after being mixed with excipients prior to contacting the control agent.

The active-containing formulation of the present invention is characterized as being substantially alkali-soluble and substantially acid-insoluble. These properties advantageously delay the usually immediate release of active in the acid environment of the upper gastrointestinal tract and, allow release of active in the alkaline environment of the lower gastrointestinal tract.

Suitable alkali-soluble and acid-insoluble polymers include cellulose phthalates, polyvinyl phthalates, cellulose succinates, cellulose butyrates, poly(meth)acrylic acids and partially esterified poly(meth)acrylic acids. Preferred agents are cellulose phthalates and partially esterified poly(meth)acrylic acids.

The use of "meth" as a prefix in parenthesis for the (meth)acrylic copolymers indicates that the polymer molecule is derived from one or both of acrylic and methacrylic species. Thus, the copolymer can be derived from partially esterified acrylic acid and methacrylic acid in which the ester groups are methyl and ethyl. Other conventional comonomers may be present in the copolymers as long as they do not detract from the copolymer's usefulness in the present system.

A particularly suitable release-control agent is that sold by FMC Corporation, Philadelphia, Pa. under the name of Aquacoat® ECD-30, this being in the form of a 30% aqueous dispersion of ethyl cellulose having a low particle size and a narrow particle size distribution. Also useful is Eudragit L30D, a copolymer anionic in character based on partially esterified poly(meth)acrylic acid (ratio of free carboxyl groups to esterified carboxyl groups being about 1:1) and having a mean molecular weight of about 250,000. Alternatively, molten pharmaceutically-acceptable wax such as stearic acid, stearyl alcohol, PEG 3350, etc. may be selected as the release-control agent. Mixtures of the above release-control agents are also contemplated.

The release-control agent is preferably in the form of an aqueous suspension, an aqueous emulsion, an aqueous dispersion, water containing organic solvent, or organic solution.

The amount of the release-control agent contained in the formulation is a key feature of the present invention. It has been discovered that the ratio of the active ingredient, here gemfibrozil, to the release-control agent contacted under conditions suitable for granulation can be used to provide desired release characteristics for the resultant product. For example, when granulation of the active is undertaken using an aqueous dispersion of a release-control agent such as Aquacoat®, the result is that some of the granules formed will have sustaining properties while other granules will not. This is believed to be as a result of the amount of release-control agent available for intimate contact with the active particles. The ratio of release-control agent to active ingredient under granulation conditions provides a composition whereby the active is free or partially-free of release-control agent and wherein a certain amount of active is bound to the release-control agent.

Depending on the ratio of active to release-control agent, the release pattern of the active can be exquisitely tailored over a broad range of release periods. For example, when the ratio of the active to the release-control agent is relatively high, the release rate is relatively low since a small portion of the active will be coated with a large quantity of the release control agent as the granulation is formed. The inverse of this relationship is also true. When the ratio of the active to the release-control agent is relatively low, the amount of drug released per unit time is relatively high. Between these two relative extremes, a complete spectrum of predictable release profiles is possible.

In one embodiment the ratio of gemfibrozil to the release-control agent is from about 11:0.5 to about 11:5 by weight. In a preferred embodiment, the ratio of gemfibrozil to the release-control agent is from about 11:0.75 to about 11:3 by weight, while in a most preferred embodiment, the ratio is from about 11:0.85 to about 11:1.25 by weight. The above ratios provide formulations which conveniently allow once a day dosing.

The gemfibrozil particles may also be blended with excipients such as cellulose derivatives or lactose prior to granulation with the release-control agent. In a preferred embodiment, the cellulose derivatives include materials such as microcrystalline cellulose, water-soluble hydroxyalkyl celluloses and mixtures thereof.

The formulation may also contain one or more processing aids such as separating agents, plasticizers, stabilizers, lubricants and the like which can be present in relatively minor amounts. Useful separating or anti-tackiness agents include kaolin, talc, magnesium trisilicate, silicon dioxide, calcium carbonate and the like. Talc is preferred. Lubricants including magnesium stearate, calcium stearate, zinc stearate, colloidal silicon dioxide, stearic acid, and polyethylene glycol also can be added to assist in the formulation. In addition, the formulation may also include a disintegration excipient. Suitable disintegration excipients include one or more water dispersable cellulose derivatives such as microcrystalline cellulose, sodium croscarmellose, starch, starch derivatives such as sodium carboxymethylstarch, and cross-linked polyvinyl pyrrolidone. Coloring agents may also be included if desired.

The particle size (diameter) of the granulation may range from 10 to about 325 mesh and preferably from about 20 to about 200 mesh. The gemfibrozil formulation may then be compressed into tablets or included in capsules and the like depending on the preference of the artisan. In addition, depending upon the particular excipients selected, the resultant dosage forms may be prepared so that the dosage form maintains its shape, slightly or substantially disintegrates or erodes after ingestion.

In accordance with a further embodiment, there is provided a method of preparing the novel gemfibrozil formulation. The method includes contacting gemfibrozil particles, preferably finely divided, with a release-control agent such as one of the agents described herein in an amount sufficient to provide both immediate and controlled release of the active from the formulation. Preferably, the contacting of the gemfibrozil with the release-control agent is carried out by granulation with the ingredients present in the ratios set forth above.

EXAMPLES

The following examples serve to provide further appreciation of the invention but are not meant in any way to restrict the effective scope of the invention.

Example 1

A granulation containing the following ingredients was prepared:

| Ingredients | Weight (grams) |
| --- | --- |
| Gemfibrozil | 600.00 |
| Microcrystalline Cellulose NF, Powder | 60.00 |
| Aquacoat ® ECD-30 (30% solids) | 184.45 |
| Triethyl Citrate | 18.44 |
| Syloid 244 | 2.21 |
| Antifoam AF Emulsion | 0.21 |
| Purified Water | 12.00 |
| To Make | 736.20 |

The granulation was prepared by mixing gemfibrozil and microcrystalline cellulose in a 600 L Collette Gral for about two minutes with a mixer at low speed until a uniform mixture of the ingredients was obtained. Separately, the Antifoam AF Emulsion and triethyl citrate were dispersed in the Aquacoat® ECD-30 (30% solids) using a Lightnin ® mixer; Syloid 244 was then added to the dispersion and stirring was continued. The dispersion was then added to the mixture in the Gral while mixing. Mixing was continued after the addition of the dispersion for two minutes with the granulator on medium speed. After the release-control agent was evenly distributed, purified water was added to make a granulation. The mixture was wetted for approximately another two minutes to obtain a heavy granulation. Thereafter, the granulation was spread on paper lined trays and dried in a forced air oven at 45° C. overnight. The granulation was passed through a Fitz mill using a #2AA RH screen at medium speed. The resultant granulation had a particle size of about 20–200 mesh and flowed readily.

Example 2

Controlled release tablets containing gemfibrozil were prepared according to the following formula:

| | Weight (grams) |
| --- | --- |
| Tablet Blend | |
| Granulation from Example 1 | 736.20 |
| Microcrystalline Cellulose NF, Granular | 44.55 |
| Croscarmellose Sodium NF, type A | 43.00 |
| Syloid 244 | 21.25 |
| Calcium Stearate | 5.00 |
| To Make | 850.00 |
| Tablet Film Coating | |
| Color Coat Opadry Pink Y-5-1421-G | 41.67 |
| Antifoam AF Emulsion, Medical | 0.83 |
| Purified Water | 374.17 |
| To Make about | 892.50 |
| Tablet Polishing | |
| Purified Water | 21.25 |
| Candelilla Wax, FCC, Powdered | 0.42 |
| To Make about | 892.92 |

A 20 cu.ft. P-K blender was charged with the granulation along with microcrystalline cellulose and croscarmellose sodium. The ingredients were tumble blended for about five minutes.

A portion of the granulation was removed from the blender and tumble mixed for five minutes with Syloid 244 and calcium stearate. The resulting mixture was then passed through a 20 # screen and returned to the blender. Mixing was continued for another five minutes. The resultant granulation was then compressed into tablets weighing about 850 milligrams. The tablets were then film coated with 10% w/w solution of Opadry ® in a 48" Accela Cota ® machine and then polished with candelilla wax, to provide the finished product with a smooth outer coat.

Example 3

In this example, dissolution of the film coated tablets prepared as a result of Example 2 was demonstrated by dissolving the tablets in a solution having 0.2M phosphate buffer and an alkaline pH of 7.5, as a model of the prevailing conditions of the lower G.I. tract. The results of the tests conducted using the product of Example 2 are set forth in the Table below.

TABLE

Dissolution of film coated tablets in pH 7.5, 0.2M phosphate buffer.

| Time (Hours) | Percent (%) Gemfibrozil Released |
| --- | --- |
| 0.25 | 52.9 |
| 0.5 | 65.7 |
| 0.75 | 72.0 |
| 1 | 76.2 |
| 2 | 85.7 |
| 4 | 93.1 |
| 6 | 96.3 |

Referring to the Table, it can be seen that even though the release-control agent was in contact with the active, the release of the active was not fully accomplished until after six hours in the dissolution media. This release pattern was also shown to be very gradual after an initial load of the active was released. This smooth onset and predictable delivery pattern allows the artisan to provide a gemfibrozil formulation demonstrating both immediate and controlled release.

While there have been described what are presently believed to be the preferred embodiments of the invention, those skilled in the art will realize that changes and modification may be made thereto without departing from the spirit of the invention, and it is intended to claim all such changes and modifications as fall within the true scope of the invention.

What is claimed is:

1. A method of preparing a formulation of gemfibrozil having both immediate and controlled release of said gemfibrozil, comprising:
   (a) providing gemfibrozil particles;
   (b) adding a release-control agent which is a pH neutral polymer to the gemfibrozil particles wherein the ratio of said gemfibrozil particles to said release-control agent is form about 11:0.5 to about 11:5 by weight of said dispersion to provide both immediate and controlled release of said gemfibrozil;
   (c) mixing the gemfibrozil particles and the release-control agent; and
   (d) granulating the mixture of the gemfibrozil particles and the release-control agent to provide a formulation consisting of a single granulation.

2. The method of claim 1, wherein said release-control agent is selected from the group consisting of cellulose phthalates, ethyl cellulose, polyvinyl phthalates, cellulose succinates, cellulose butyrates, poly(meth)acrylic acids, partially esterified poly(meth)acrylic acids and mixtures thereof.

3. The method of claim 2, wherein said gemfibrozil particles are finely divided.

4. The method of claim 3 wherein the ratio of said gemfibrozil to said release-control agent is from about 11:0.75 to about 11:3 by weight.

5. The method of claim 4, wherein the ratio of said gemfibrozil to said release-control agent is from about 11:0.85 to about 11:1.25 by weight.

6. The method of claim 5, wherein said gemfibrozil particles are blended with a water-disintegratable binder prior to being granulated with said release-control agent.

7. The method of claim 6, wherein said water-disintegratable binder is selected from the group consisting of cellulose derivatives, lactose and mixtures thereof.

8. The method of claim 7, wherein said cellulose derivatives are selected from the group consisting of microcrystalline cellulose, water soluble hydroxyalkyl celluloses and mixtures thereof.

9. The method of claim 1 further comprising milling said granulation to a particle size of from about 10 to about 325 mesh.

10. The method of claim 9, further comprising milling said granulation to a particle size of from about 20 to about 200 mesh.

11. A method of preparing a compressed tablet formulation of gemfibrozil having immediate and controlled release of said gemfibrozil comprising:
   (a) providing gemfibrozil particles;
   (b) blending the gemfibrozil particles with a water-disintegratable binder;
   (c) adding a dispersion comprised of a release-control agent which is a partially esterified poly(meth)acrylic acid to the gemfibrozil particles wherein the ratio of said gemfibrozil to said release-control agent is from about 11:0.5 to about 11:5 by weight of said dispersion to provide both immediate and controlled release of said gemfibrozil;
   (d) mixing the gemfibrozil particles and the release-control agent;
   (e) granulating the mixture to provide a formulation consisting of a single granulation; and
   (f) compressing the formulation obtained as a result of steps (a)–(e) hereinabove into a tablet form.

\* \* \* \* \*